(12) United States Patent
Xu

(10) Patent No.: US 10,594,876 B2
(45) Date of Patent: Mar. 17, 2020

(54) READING APPARATUS WITH COLORIMETRY UNIT AND REFERENCE SURFACE THAT COOLS SHEET

(71) Applicant: KONICA MINOLTA, INC., Chiyoda-ku, Tokyo (JP)

(72) Inventor: Tianzi Xu, Hino (JP)

(73) Assignee: KONICA MINOLTA, INC., Chiyoda-Ku, Tokyo (JP)

(*) Notice: Subject to any disclaimer, the term of this patent is extended or adjusted under 35 U.S.C. 154(b) by 0 days.

(21) Appl. No.: 15/939,773

(22) Filed: Mar. 29, 2018

(65) Prior Publication Data

US 2018/0288240 A1 Oct. 4, 2018

(30) Foreign Application Priority Data

Mar. 30, 2017 (JP) ................. 2017-067975

(51) Int. Cl.
*H04N 1/00* (2006.01)
*G01J 3/50* (2006.01)
(Continued)

(52) U.S. Cl.
CPC ............ *H04N 1/00087* (2013.01); *G01J 3/50* (2013.01); *G01N 21/274* (2013.01);
(Continued)

(58) Field of Classification Search
CPC .......... H04N 1/00087; H04N 1/00615; H04N 1/00989; H04N 1/00602; H04N 1/00034;
(Continued)

(56) References Cited

U.S. PATENT DOCUMENTS 5,151,743 A * 9/1992 Yaguchi ............... G03G 15/201
219/216
2005/0006562 A1 1/2005 Sugihara et al.
(Continued)

FOREIGN PATENT DOCUMENTS

CN 102221800 A 10/2011
CN 103913970 A 7/2014
(Continued)

OTHER PUBLICATIONS

Office Action (Notification of Reasons for Refusal) dated Feb. 26, 2019, by the Japan Patent Office in corresponding Japanese Patent Application No. 2017-067975 and English translation of the Office Action. (18 pages).
(Continued)

*Primary Examiner* — Christopher Wait
(74) *Attorney, Agent, or Firm* — Buchanan Ingersoll & Rooney PC

(57) ABSTRACT

A reading apparatus that performs colorimetry for an image on a sheet, includes a conveyor that conveys the sheet along a conveyance path; a first guide member that includes a reference surface arranged to face the conveyance path and to oppose the sheet and provided with an opening, and, guides the sheet; a first opposite member that urges the sheet toward the reference surface, and, brings the sheet in contact with the reference surface; a colorimetry unit that is disposed at a side opposite to the conveyance path so as to sandwich the first guide member, and, performs colorimetry for the image through the opening; and a processor that controls the conveyor and the first opposite member so as to convey the sheet in a state of being brought in contact with the reference surface, before the colorimetry unit performs colorimetry for the image.

20 Claims, 11 Drawing Sheets

(51) Int. Cl.
*H04N 1/60* (2006.01)
*G01N 21/27* (2006.01)
*G01J 3/52* (2006.01)

(52) U.S. Cl.
CPC ..... *H04N 1/00034* (2013.01); *H04N 1/00045* (2013.01); *H04N 1/00602* (2013.01); *H04N 1/00615* (2013.01); *H04N 1/00989* (2013.01); *H04N 1/6033* (2013.01); *G01J 3/524* (2013.01)

(58) Field of Classification Search
CPC ............. H04N 1/00045; H04N 1/6033; G01N 21/274; G01J 3/50; G01J 3/524
See application file for complete search history.

(56) References Cited

U.S. PATENT DOCUMENTS

| | | | |
|---|---|---|---|
| 2011/0255887 A1 | 10/2011 | Kato et al. | |
| 2012/0147388 A1* | 6/2012 | Kojima | B65H 5/062 358/1.1 |
| 2013/0094041 A1 | 4/2013 | Takemura | |
| 2013/0222858 A1* | 8/2013 | Yokoyama | G06K 15/1878 358/2.1 |
| 2013/0243451 A1 | 9/2013 | Hirota et al. | |
| 2014/0185047 A1* | 7/2014 | Tajima | G01J 3/46 356/402 |

FOREIGN PATENT DOCUMENTS

| | | |
|---|---|---|
| JP | H02-305169 A | 12/1990 |
| JP | H03-203456 A | 9/1991 |
| JP | H07-212545 A | 8/1995 |
| JP | 2000-177880 A | 6/2000 |
| JP | 2005-033299 A | 2/2005 |
| JP | 2011-091473 A | 5/2011 |
| JP | 2013-054324 A | 3/2013 |
| JP | 2013-088614 A | 5/2013 |
| JP | 2016-191779 A | 11/2016 |

OTHER PUBLICATIONS

Office Action dated May 24, 2019, by the Chinese Patent Office in corresponding Chinese Patent Application No. 201810269884.9 and English translation of the Office Action. (32 pages).

Office Action (Notice of Reasons for Refusal) dated Jun. 18, 2019, by the Japanese Patent Office in corresponding Japanese Patent Application No. 2017-067975 and English translation of the Office Action. (17 pages).

Chinese Office Action dated Oct. 12, 2019 issued in corresponding Chinese Patent Application No. 201810269884.9, with English translation (26 pages).

\* cited by examiner

A-A'

B-B'

C-C'

READING APPARATUS WITH COLORIMETRY UNIT AND REFERENCE SURFACE THAT COOLS SHEET

CROSS-REFERENCE TO RELATED APPLICATION

The entire disclosure of Japanese patent application No. 2017-067975, filed on Mar. 30, 2017, is incorporated herein by reference in its entirety.

BACKGROUND

1. Technical Field

The present invention relates to a reading apparatus, an image forming system, and a non-transitory computer-readable storage medium storing a control program.

2. Description of Related Arts

In recent years, in the color printing industry, in place of conventional offset-printing apparatuses, image forming apparatuses, such as a printer of an electrophotographic system, have been utilized widely.

In such an image forming apparatus, in order to attain stabilization of image density, there is an image forming apparatus that disposes an optical sensor on a conveyance path of a sheet, detects a state of an image on the basis of reflected light read by the optical sensor, and, feeds back the state of the image to an image forming condition (for example, Patent Literature 1 (Japanese Patent 2000-177880A)).

In the image forming apparatus disclosed by the Patent Literature 1, there are provided a first sheet guide provided with an opening at a reading position of the optical sensor and a second sheet guide to which a spring opposite to the first sheet guide is attached. Then, when a sheet thicker than a gap between the first and second sheet guides passes through the gap between the both guides, the second sheet guide is retracted, and the sheet is pressed against the first sheet guide with a spring. With this, the reading accuracy is prevented from deteriorating due to inclination or waving of a sheet to be read.

Furthermore, in order to stabilize image color and a line forming position with high accuracy, an image forming apparatus has appeared that disposes a scanner using a CCD line sensor and a spectral colorimeter to measure spectral reflectance on a conveyance path of sheets, and that feeds back image data obtained from the scanner to an image forming condition (Patent Literature 2 (Japanese Patent 2016-191779A)).

In the image forming apparatus disclosed by the Patent Literature 2, a test chart formed on a sheet is read by both the scanner and the spectral colorimeter, and, by comparing the obtained color data, the absolute value of the colorimetry value with the scanner is guaranteed.

SUMMARY

However, in the case where an image forming apparatus uses toner, in order to fix toner on a sheet, a heating process by a fixing device is needed. Moreover, in the case where an image forming apparatus is of an inkjet system, a heating process for drying ink is needed.

A sheet which has been heated in the heating process and has a high temperature, changes in color due to thermochromism phenomenon. Accordingly, even if color on the sheet in such a state is measured, since the state is different from a state where a user visually observes (that is, a room temperature), color measurement may not be performed accurately.

The present invention has been achieved in view of the above-mentioned circumstances, and an object of the present invention is to provide a reading apparatus that performs colorimetry with high accuracy. To achieve at least one of the above-mentioned objects, according to an aspect of the present invention, a reading apparatus reflecting one aspect of the present invention that performs colorimetry for a sheet output from an image forming apparatus with a print surface on which an image is printed, includes: a conveyor that conveys the sheet along a conveyance path; a first guide member that includes a reference surface arranged to face the conveyance path and to oppose the print surface of the sheet and provided with an opening, and, guides the sheet conveyed on the conveyance path; a first opposite member that urges the sheet conveyed on the conveyance path toward the reference surface, and, brings the sheet in contact with the reference surface; a colorimetry unit that is disposed at a side opposite to the conveyance path so as to sandwich the first guide member, and, performs colorimetry for the image through the opening; and a processor that controls the conveyor and the first opposite member so as to convey the sheet in a state of being brought in contact with the reference surface of the first guide member, before the colorimetry unit performs colorimetry for the image.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention.

DETAILED DESCRIPTION OF EMBODIMENTS

Figure 1:
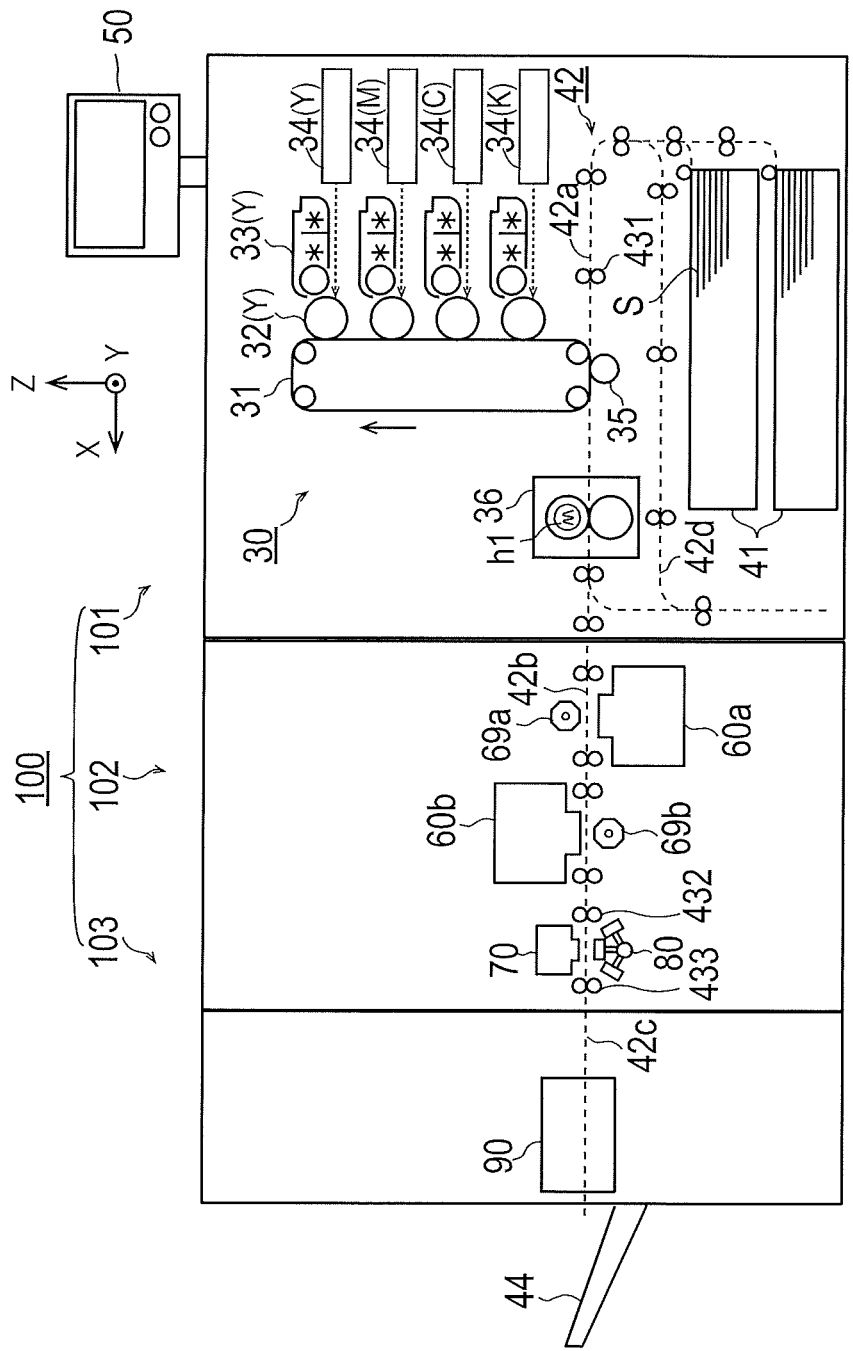
FIG. 1 is a cross sectional view showing a schematic constitution of an image forming system according to one embodiment of the present invention.

Hereinafter, one or more embodiments of the present invention will be described with reference to the drawings. However, the scope of the invention is not limited to the disclosed embodiments. In the description for the drawings, the same constituent is provided with the same code, and the overlapping description is omitted. Moreover, the dimensional ratios in the drawing are exaggerated on account of description, and, may be different from the actual ratios. In the drawings, the vertical direction is set to the Z direction, the front/rear direction in the image forming system is set to the Y direction, and a direction orthogonal to each of the Z and Y directions is set to the X direction. Furthermore, hereinafter, the X direction may be referred to as a conveyance direction, and the Y direction may be referred to as a width direction or a main scanning direction.

Figure 2:
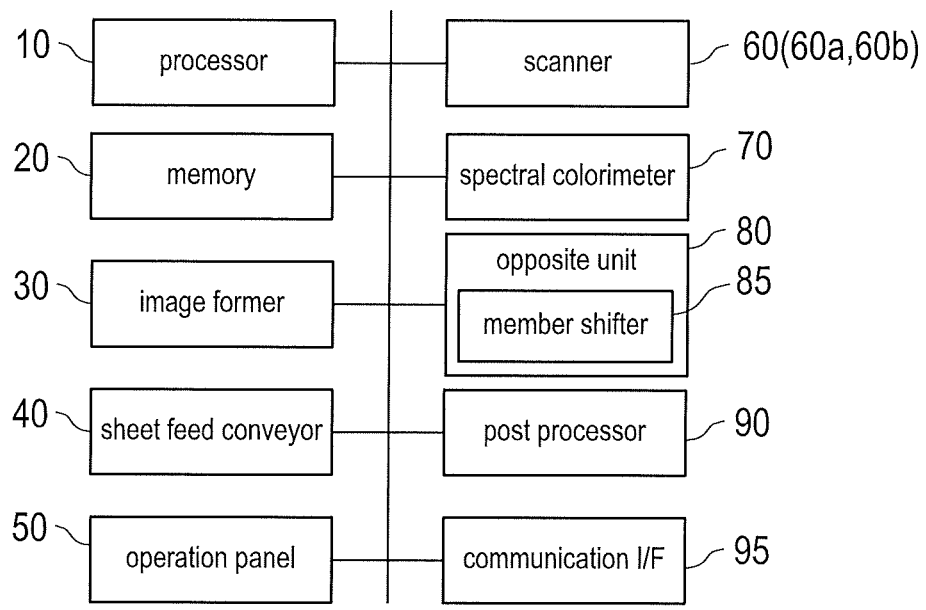
FIG. 2 is a block diagram showing a hardware constitution of an image forming system.

FIG. 1 is an illustration showing a schematic constitution of an image forming system according to one embodiment of the present invention. FIG. 2 is a block diagram showing a hardware constitution of the image forming system.

As shown in FIG. 1 and FIG. 2, an image forming system 100 includes an image forming apparatus 101, a reading apparatus 102, and a post processing apparatus 103. The reading apparatus 102 includes a plurality of colorimetry units of scanners 60a and 60b and a spectral colorimeter 70. The image forming apparatus 101 performs printing for sheets (paper sheets). The reading apparatus 102 performs colorimetry for the sheets printed by the image forming apparatus 101, and the post processing apparatus 103 performs post processing for the printed sheets.

As shown in FIG. 2, the image forming system 100 includes a processor 10, a memory 20, an image former 30, a sheet feed conveyor 40, an operation panel 50, scanners 60a and 60b, a spectral colorimeter 70, an opposite unit 80, a post processor 90, and a communication I/F (interface) 95, and these devices are connected with each other through buses for exchanging signals.

The processor 10 includes a CPU, and, performs control for each device of an apparatus and various kinds of arithmetic processing in accordance with programs. Moreover, the processor 10 has a function to adjust the color of images and image formation positions on the basis of image data obtained by the reading of the scanner 60a (or scanner 60b). Examples of color adjustment for images include adjustment of LUT for color conversion on the basis of image data (image signals) acquired by reading images of a color chart, and adjustment of image formation conditions of the image former 30. Examples of image position adjustment include the adjustment of image formation position on the basis of the detected positions of edges and trim marks (also, referred to as registration marks and mark images) of a sheet.

The memory 20 includes a ROM that stores various programs and various kinds of data beforehand, a RAM that memorizes programs and data temporarily as a work area, and a hard disk that stores various programs and various kinds of data. The memory 20 stores image data for color charts in which color patches of multiple colors for various evaluations are arranged, a control table for the pressing forces of the opposite unit 80 for paper information mentioned later, and the like.

The image former 30 includes an intermediate transfer belt 31, a photoconductor drum 32, a developer 33, a writer 34, a secondary transferer 35, and a fixer 36. Each of the photoconductor drum 32, the developer 33, and writer 34 includes the constitution corresponding to the respective basic colors of yellow (Y), magenta (M), cyan (C), and black (K). In FIG. 1, with regard to these basic colors, the notations of symbols other than Y are omitted. The fixer 36 includes a hollow heating roller in the inside of which a heater h1 is disposed, and a pressure applying roller which opposes the heating roller. Each roller is controlled to become a predetermined temperature (for example, 100° C. or more) by the heater h1, and, applies heating and pressing processes to a sheet.

The writer 34 of the image former 30 exposes the charged surface of the photoconductor drum 32 on the basis of image data, and, forms an electrostatic latent image. In the developer 33, the formed electrostatic latent image is developed with the toner of the developer 33, and the toner image of each of the basic colors is formed on the surface of a corresponding one of the photoconductor drums 32. The toner images of the basic colors are superimposed on one after another on the intermediate transfer belt 31 via the respective primary transferers (not shown) corresponding to the colors, whereby a full color toner image is formed. This toner image is transferred on a sheet S via the secondary transferer 35, and thereafter, is subjected to the heating and pressing processes in the fixer 36, whereby a full color image is formed on the sheet S.

(Sheet Feed Conveyor 40)

The sheet feed conveyor 40 includes a sheet feed tray 41, a conveyance path 42 (42a to 42d), a plurality of conveyance rollers 431 to 433, a drive motor (not shown) to drive these rollers, and a sheet delivery tray 44.

The sheet feed conveyor 40 rotates each of the conveyance roller 431 to 433 at a predetermined timing by the drive of the drive motor, feeds out sheets S from the sheet feed tray 41, and conveys the sheets S in the conveyance path 42.

The conveyance path 42 includes conveyance paths 42a and 42d in the image forming apparatus 101, a conveyance path 42b in the reading apparatus 102, and a conveyance path 42c in the post processing apparatus 103.

The sheet S fed out from the sheet feed tray 41 is conveyed on the conveyance path 42a. On the conveyance path 42a, a registration roller 431 to adjust a conveyance timing of a sheet by rotating and stopping by a clutch is disposed.

The sheet S that has been conveyed on the conveyance path 42a and has been subjected to image formation by the image former 30, is subjected to respective processes correspondingly to print settings of a print job via the conveyance path 42b, 42c, subsequently, is delivered to the outside of the apparatus, and then is placed on a sheet delivery tray 44.

Moreover, in the case where the print setting of the print job is the setting for both-side printing, the sheet S on one side (a first surface) of which the image formation has been preformed, is conveyed to an ADU conveyance path 42d located on the lower side of the image forming apparatus 101. The sheet S having been conveyed to this ADU conveyance path 42d is conveyed to a switch back route so that the front surface and back surface of the sheet is reversed, and thereafter, the sheet S joins the conveyance path 42a, and is subjected again to image formation onto another surface (a second surface) in the image former 30.

(Operation Panel 50)

The operation panel 50 includes a touch panel, a ten key, a start button, a stop button, etc., and is used for inputting various kinds of settings, such as, printing conditions and an execution timing of color adjustment, displaying the state of apparatus, and inputting various kinds of instructions. Moreover, a user can input sheet information with respect to sheets loaded in the sheet feed tray 41 through the operation panel 50. Examples of the sheet information include the kind of sheet (a regular sheet, a coated sheet, etc.), and the thickness, weight, size, etc. of sheet. The input sheet information is correlated with the sheet feed tray 41, and then, is memorized in the memory 20.

(Scanners 60a and 60b)

The scanners 60a and 60b are disposed on the conveyance path 42b so as to sandwich this conveyance path 42b and to read images on the different surfaces of the sheet S respectively. In the case of the setting for both-side printing, the scanner 60b performs reading for the image on the upper side surface (the above-mentioned second surface) of the sheet S, and the scanner 60a performs reading for the image on the lower side surface (the above-mentioned first surface). In the case of the setting for one side printing, only the scanner 60b performs reading for the image on the front surface side of the sheet S.

The processor 10 performs color adjustment and image position adjustment on the basis of image data acquired by the scanner 60a or the scanner 60b. The scanners 60a and 60b are provided with back surface units 69a and 69b respectively at positions to face them across the conveyance path 42b. The scanner 60a and the scanner 60b are configured with the same constitution. Moreover, the back surface unit 69a and the back surface unit 69b are also configured with the same constitution. Hereinafter, description is given for the scanner 60a and the back surface unit 69a, and the description for the scanner 60b and the back surface unit 69b is omitted.

The scanner 60a includes a sensor array, a lens optical system, an LED (Light Emitting Diode) light source, and a casing to store these components.

The sensor array is a color line sensor in which a plurality of optical elements (for example, CCD (Charge Coupled Device)) are arranged in the form of a line along a main scanning direction, and its reading region in the width direction corresponds to the entire width of the sheet S. The optical system includes a plurality of mirrors and a lens. The light from the LED light source passes through a document glass, and, irradiates the surface of the sheet S that passes through the reading position on the conveyance path 42b. The image at this reading position is led by the optical system, and, forms an image on the sensor array.

The back surface unit 69a is a rotatable member in the form of a polygonal pillar has a polygonal (for example, hexagon) cross sectional shape, and its rotation axis is arranged along the main scanning direction of the scanner 60a. On the surfaces of the polygonal pillar, a white surface, a black surface, and a reference color surface for shading correction are formed, and in the case of performing reading for an image on the sheet S, the white surface is made to face the scanner 60a. In the case of detecting the edge of a white sheet S, the black surface is made to face the scanner 60a, and, in the case of performing shading correction, the reference color surface is positioned so as to face the scanner 60a.

(Spectral Colorimeter 70)

The spectral colorimeter 70 is disposed on the conveyance path 42b in the X direction. Moreover, in the Z direction, the spectral colorimeter 70 is arranged on the side opposite to the conveyance path 42b across the first guide plate 471 (a first guide member) (refer to FIG. 3 mentioned later). The spectral colorimeter 70 spectrally measures the color of each of the color patches of an image for color evaluation formed on a sheet S by the image former 30, and, can acquire spectral reflectance of each wavelength in a visible light region and in its neighborhood region. The colorimetry data can be output in a color system, such as XYZ. Each of the color patches of this evaluation image is similarly read by the scanner 60a or the scanner 60b as mentioned later, and the read data is converted into the data of the same color system, such as the XYZ. Then, by comparing the both data, the calibration for the scanners 60a and 60b are performed (determination of correction values).

The size and shape of the reading area of the spectral colorimeter 70 (hereafter, referred to as a "colorimetry region a1") is a circle of about 4 mm on the surface (XY plane) of the sheet S. The position (in the Z direction) is separated by ten and several millimeters (for example, about 15 mm) from the undersurface of the spectral colorimeter 70. Moreover, in the width direction, the colorimetry region a1 of the spectral colorimeter 70 is set to, for example, the center of the sheet S to be conveyed, and this area is included in the reading region of the scanners 60a and 60b.

As shown in FIG. 1, the spectral colorimeter 70 is disposed on the downstream side in the conveyance direction than the scanners 60a and 60b within the conveyance path 42b. In order to avoid the influence by thermochromism phenomenon, it is desirable to dispose the spectral colorimeter 70 at a position separated further away from the fixer 36 such that the temperature of the sheet S heated by the fixer 36 becomes close to a room temperature (temperature when a user views) at the time of performing colorimetry. However, without being restricted to this, the spectral colorimeter 70 may be disposed on the upstream side than the scanners 60a and 60b within the conveyance path 42b.

(Post Processor 90)

The post processor 90 is disposed on the conveyance path 42c. The post processor 90 includes, for example, a stapler that performs binding processing and a stacker that stacks sheets, and, piles up a plurality of sheets S with this stacker, and thereafter, performs side stitching processing using staples with the stapler. A bundle of sheets S having been subjected to the side stitching are delivered on the sheet delivery tray 44. Moreover, the sheets S having been not subjected to the side stitching are delivered via the conveyance path 42*c* as they are.

(Communication Interface 95)

As the communication interface 95, various kinds of local connecting interfaces, for example, network interfaces according to standards such as SATA, PCI ExpreS, USB, Ethernet (registered trademark), and IEEE 1394, and wireless-communications interfaces such as Bluetooth (registered trademark), and IEEE802.11, etc. may be used. A print job including print data and print setting is received from external terminals, such as PC through the communication interface 95.

(Opposite Unit 80)

Figure 3:
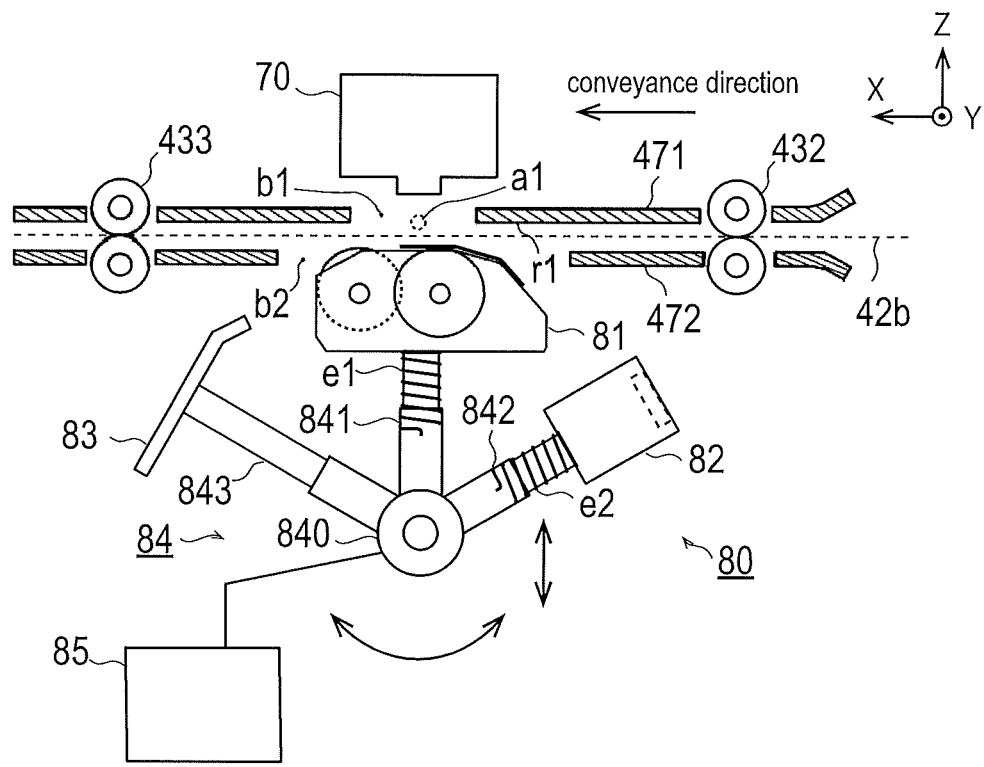
FIG. 3 is an illustration showing a constitution of a spectral colorimeter and an opposite unit of a reading apparatus according to the first embodiment.

Next, with reference to FIG. 3 through FIG. 12, description is given for the constitution of an opposite unit 80 in the reading apparatus 102 relating to the first embodiment. FIG. 3 is an illustration showing the constitution of the spectral colorimeter 70 and the opposite unit 80, and, is a figure in which a part of FIG. 1 is enlarged.

As shown in FIG. 3, the opposite unit 80 includes a first opposite member 81, a second opposite member 82, a third opposite member 83, a holding member 84 holding these members, and a member shifter 85.

The holding member 84 includes a rotation shaft 840, pillars 841 to 843 disposed on this, and elastic members e1 and e2. The first opposite member 81, the second opposite member 82, and the third opposite member 83 are held at the tip sides of the pillars 841 to 843 respectively. The first opposite member 81 attached to the pillar 841 is urged toward the tip side with the elastic member e1. The pillar 841 can expand and contract within a predetermined range, and in the case where the first opposite member 81 at the tip comes in contact with the first guide plate 471, the pillar 841 contracts a little against the elastic member e1. Similarly, the second opposite member 82 is also attached to the pillar 842 which can expand and contract, and, is urged toward the tip side with the elastic member e2. The first opposite member 81 is used as a background when performing the colorimetry for an image on a sheet S by the spectral colorimeter 70. The second opposite member 82 is used for calibration for the spectral colorimeter 70. When the spectral colorimeter 70 is not being used, the third opposite member 83 closes an opening b2 of a second guide plate 472 (a second guide member) so as not to hinder the conveyance of a sheet S, and guides the conveyance of a sheet S.

The member shifter 85 includes a transmission mechanism constituted by a drive motor, gears to transmit power from the drive motor to the rotation shaft 840, and the like (neither is illustrated), and performs a rotational shift and a vertical shift for the holding member 84. In concrete terms, the member shifter 85 rotates the rotation shaft 840 by a predetermined angle as the rotational shift so as to switch over an opposite member to be arranged at an opposite position for the spectral colorimeter 70. Moreover, as the vertical shift after the rotational shift, the member shifter 85 shifts the rotation shaft 840 vertically between a pressing position on an upper side and a retracted position on a lower side. FIG. 3 shows a state where the first opposite member 81 faces the spectral colorimeter 70 at the retracted position. Moreover, the amount of a vertical shift of the holding member 84 is changed by the member shifter 85, whereby a pressing force by the first opposite member 81 can be changed.

Moreover, a pair of guide members, i.e., first and second guide plate 471 and 472 as first and second guide members are disposed so as to sandwich the conveyance path 42*b* with a predetermined space (for example, 3 mm) therebetween and to become parallel to the X-Y plane. The first and second guide plates 471 and 472 are provided with openings b1 and b2 respectively at a position to face the colorimetry region a1 of the spectral colorimeter 70. The spectral colorimeter 70 performs colorimetry through the opening b1.

The undersurface of the first guide plate 471 on the upper side is a flat surface, and this flat surface functions as a reference surface r1. The reference surface r1 of this first guide plate 471 has a function to lead a sheet to the colorimetry region a1 and a function to cool a sheet S that has been urged and brought in contact with the reference surface r1 as mentioned later. This cooling is performed by heat conduction. Accordingly, it is desirable that the first guide plate 471 is made of materials with high heat conductivity and is configured such that a contact surface with a sheet S becomes larger. For example, the first guide plate 471 is preferably constituted by a metal flat plate, and, is more preferably constituted by a flat plate made of stainless steel material with a heat conductivity of 20.9 (W/m/K) or more.

On the other hand, at the time of cooling a sheet S, the first guide plate 471 itself is heated with the heat taken from the sheet S. The tolerance for guaranteeing the colorimetric accuracy in the height direction (Z direction) of the spectral colorimeter 70 is, for example, X±0.1 mm from the lower end of the spectral colorimeter 70 (X is any one in a range of 10 to 20 mm, and, for example, is 15 mm). Even in the case where the first guide plate 471 has expanded thermally by being heated with the heat of a sheet S, in order to enable the reference surface r1 to maintain the height of X±0.1 mm, it is preferable to use the material with a linear expansion coefficient of $60 \times 10^6$/K or less for the first guide plate 471.

(First Opposite Member 81)

Figure 4:
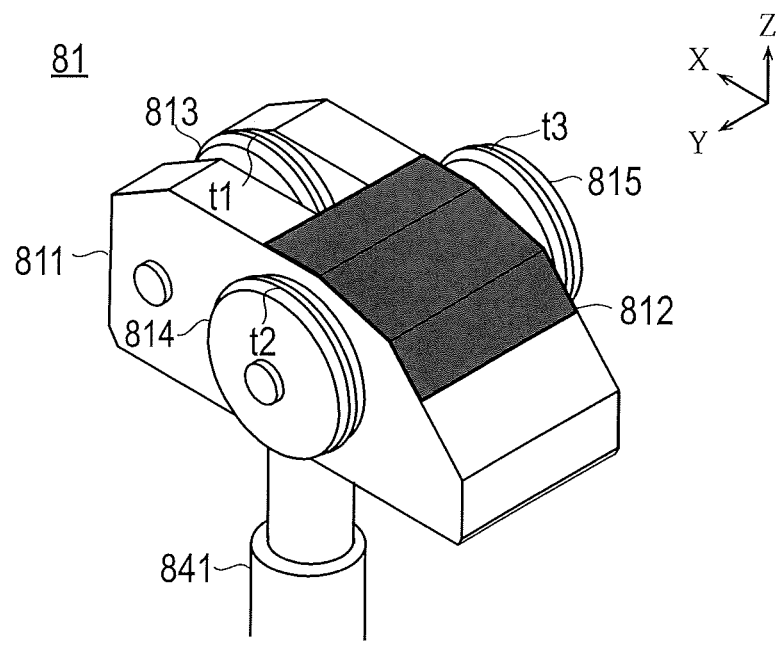
FIG. 4 is a perspective view of a first opposite member.

FIG. 4 is a perspective view of the first opposite member 81. The first opposite member 81 includes a base body 811 engaged with the pillar 841, a back face sheet 812 stuck to the base body 811, and rollers 813 to 815 that rotate together with a sheet S by coming in contact with the sheet S. Although the back face sheet 812 is indicated in gray in FIG. 4 etc., actually, the back face sheet 812 is a member with a smooth surface and color close to white, and functions as a background positioned on the back side of a sheet S at the time of colorimetry. In this connection, in place of the back face sheet 812, the surface of the base body 811 painted with white may be used.

A virtual plane formed by connecting each of the top ends t1 to t3 of the outer peripheral surfaces of the rollers 813 to 815 is parallel to the X-Y plane, and this virtual plane is located at a position slightly higher than the top surface of the back face sheet 812. For example, this virtual plane is higher by about 0.1 to 0.2 mm than the top face of the back face sheet 812. By doing in this way, as mentioned later, in the case where a sheet S is supported from its back-surface side with three contact points of the top ends t1 to t3 by point contacts, the back face sheet 812 and the sheet S become non-contact or slight contact with each other. With this, it becomes possible to prevent the back face sheet 812 from becoming dirty or worn out due to sliding friction between the back face sheet 812 and the sheet S. In the present embodiment, it is shown the example where the sheet S is supported by three points of the three rollers 813 to 815. However, without being restricted to this example, there may be provided four or more rollers for the first opposite member 81, and it may be constituted to support a sheet S by four or more points.

Figure 5:
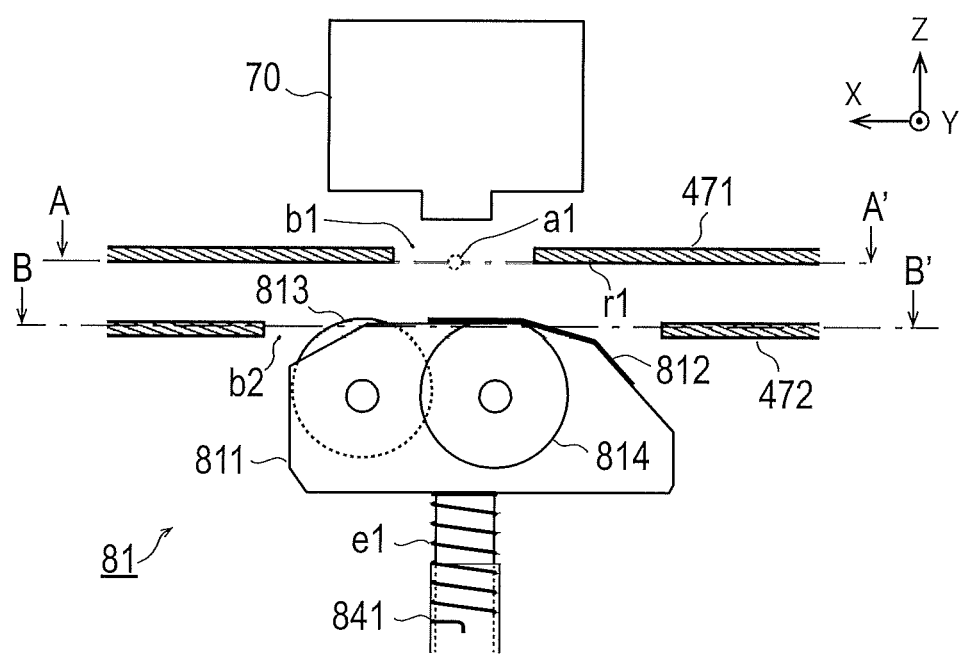
FIG. 5 is an illustration showing a first opposite member at a retracted position.
Figure 6:
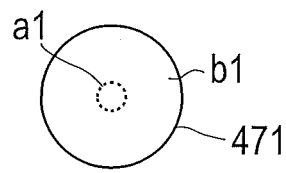
FIG. 6 is an end view showing schematically an opening of a first guide plate along an A-A' line in FIG. 5.
Figure 7:
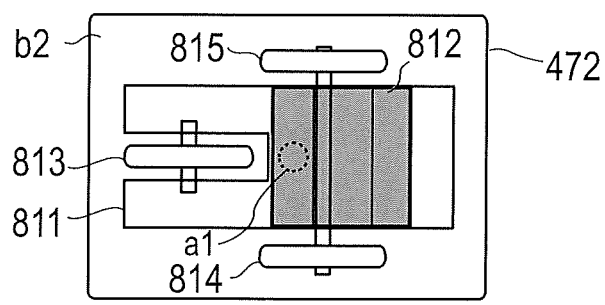
FIG. 7 is an end view showing schematically an opening of a second guide plate along an B-B' line in FIG. 5.

Next, with reference to FIG. 5 to FIG. 9, description is given for the positional relationship between the first opposite member 81 and the openings b1 and b2 at the retracted position and the pressing position. This pressing position is set up at the time of a reading mode to perform the colorimetry for a sheet S by the spectral colorimeter 70 (for example, at the time of performing later-mentioned calibration for the scanner), and the retracted position is set up at the time of a non-reading mode not to perform any colorimetry other than this (for example, later-mentioned calibration for the spectral colorimeter and adjustment for an image former). FIG. 5 is an illustration showing the first opposite member 81 located in the retracted position, and, is made by enlarging a part of FIG. 3. FIG. 6 is an end view showing schematically the opening b1 of the first guide plate 471 along the A-A' line in FIG. 5. FIG. 7 is an end view showing schematically the opening b2 of the second guide plate 472 along the B-B' line in FIG. 5.

As shown in FIG. 6, in the top view (in the Z direction), the opening b1 of the first guide plate 471 is a circular hole, and, includes the colorimetry region a1. It is preferable that the center position of the opening b1 coincides with that of the colorimetry region a1. It is preferable that, in the top view, the size of the opening b1 is several times as large as that of the colorimetric region a1. For example, in the case where the diameter of the colorimetry region a1 is 4 mm, the diameter of the opening b1 is 30 mm.

As shown in FIG. 7, the opening b2 of the second guide plate 472 is substantially rectangular. The shape and size of the opening b2 are set not to hinder the rotational shift and vertical shift of the first and second opposite member 81 and 82. In FIG. 7, in order to describe the positional relationship, the colorimetry region a1 is shown virtually.

Figure 8:
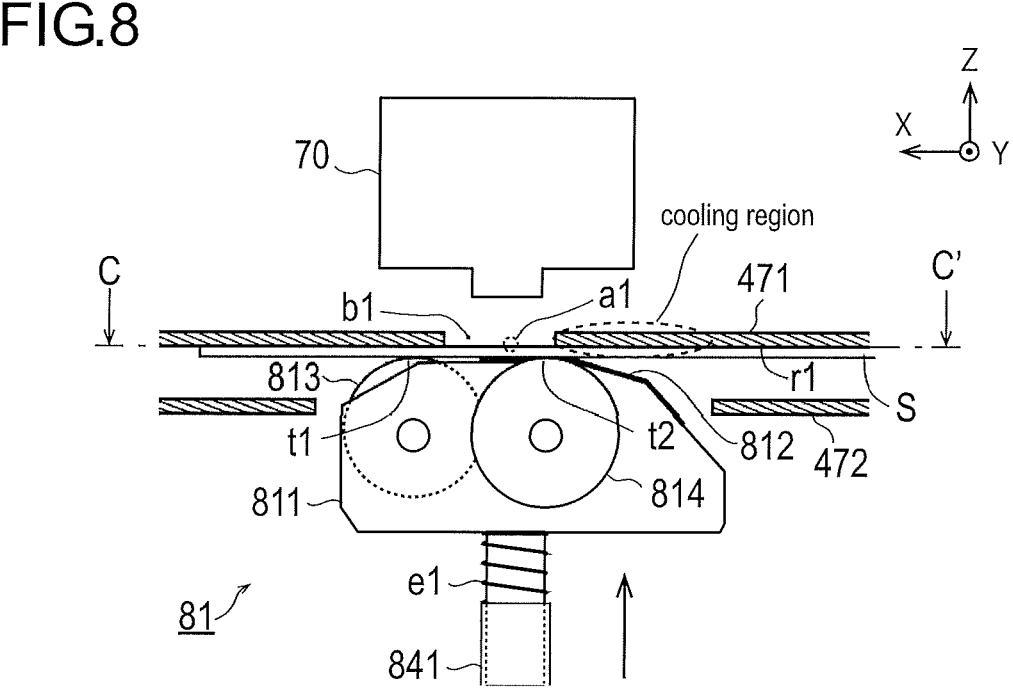
FIG. 8 is an illustration showing a first opposite member at a pressing position.
Figure 9:
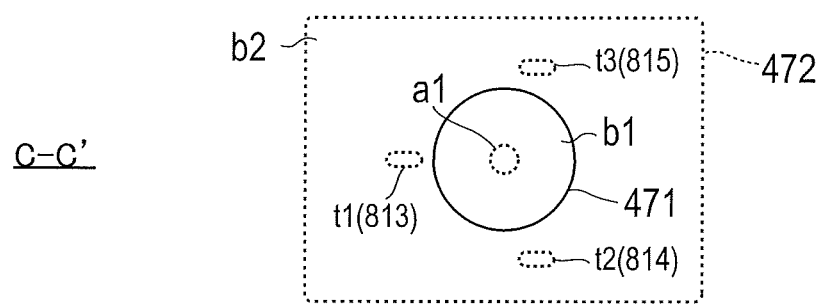
FIG. 9 is an end view showing schematically an opening of a first guide plate along a C-C' line in FIG. 8.

FIG. 8 is an illustration showing the first opposite member 81 located at the pressing position. FIG. 9 is an end view showing schematically the opening b1 of the first guide plate 471 along the C-C' line in FIG. 8. In this FIG. 9, the top ends t1 to t3 of the rollers 813 to 815 with respect to the opening b2 and the colorimetry region a1 are indicated with broken lines.

As shown in FIG. 8, the first opposite member 81 shifts to the pressing position by being moved upward by the member shifter 85. At the time of performing the colorimetry by the spectral colorimeter 70, the first opposite member 81 is located at this pressing position. Moreover, in this state, the sheet S is urged from its back-surface side by the first opposite member 81 with the elastic force of the elastic member e1 toward the reference surface r1, and, is brought in contact with the reference surface r1.

Moreover, as shown in FIG. 9, the top ends t1 to t3 to support the sheet S from the back-surface side are arranged on the outside of the opening b1 so as to surround the colorimetry region a1. In concrete terms, all or a part of the opening b1 is included in a polygonal (triangle) contact region formed by connecting these contact points. Moreover, the colorimetry region a1 is configured to be located in the vicinity of the center of the contact region. With this, it is possible to stably position the sheet S to be conveyed on the colorimetric area a1, and in addition, to stably bring the sheet S into surface contact with the reference surface r1.

The region enclosed with a broken line in FIG. 8 is a cooling region located on the upstream side in the conveyance direction than the colorimetry region a1. In the cooling region, the sheet S comes in surface contact with the reference surface r1 with a large area. With this, even if the sheet S is in a state of being quite higher than a room temperature by being heated in the fixer 36, since heat energy diffuses by heat transfer to the first guide plate 471 at a temperature close to a room temperature, the sheet S can be cooled efficiently.

In order to avoid the influence by the thermochromism, it has become clear that it is preferable to lower the temperature of the sheet S at the time of colorimetry to 30 degrees or less. In the present embodiment, the first guide plate 471 is constituted by a flat plate that is made of metal with high heat conductivity and has a flat undersurface (reference surface r1). By doing in this way, the sheet S that has been heated by the fixer 36 and has residual heat is cooled rapidly by heat conduction, whereby it becomes possible to lower the temperature of the sheet S to 30 degrees or less at the time of colorimetry. With this, it becomes possible to perform the colorimetry by the spectral colorimeter 70 stably and highly accurately without the influence of thermochromism.

(Second Opposite Member 82)

Figure 10:
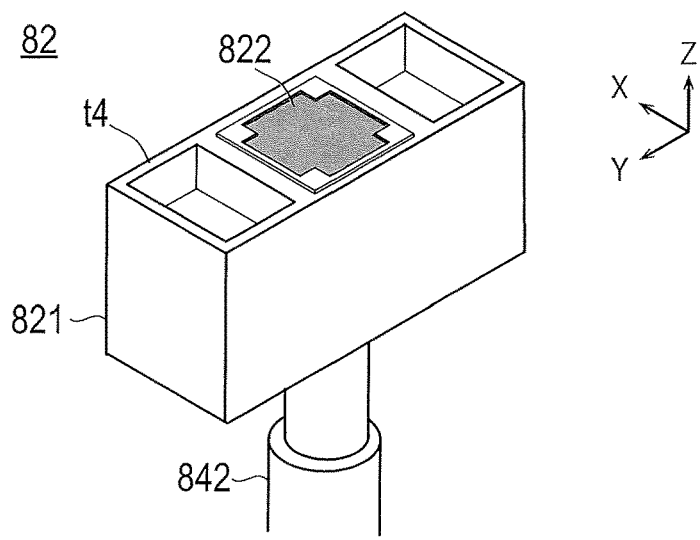
FIG. 10 is a perspective view of a second opposite member.

FIG. 10 is a perspective view of the second opposite member 82. The second opposite member 82 includes a base body 821 engaged with the pillar 842 and a reference plate 822. The height of the top end t4 of the base body 821 is set as the same height as the reference plate 822.

Figure 11:
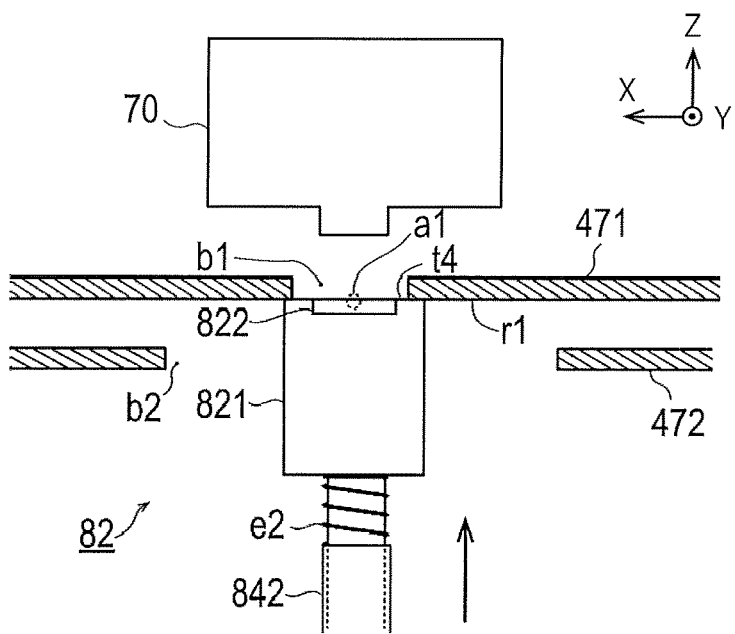
FIG. 11 is an illustration showing a second opposite member at a pressing position.

FIG. 11 is an illustration showing the second opposite member 82 located at a pressing position. The member shifter 85 shifts the second opposite member 82 to the opposite position by rotating the holding member 84, and thereafter, shifts the second opposite member 82 to the pressing position by shifting it upward. The length of the second opposite member 82 at least one of in the X direction and the Y direction is longer than the opening b1. In the pressing position, the second opposite member 82 is brought in contact with the first guide plate 471 by being urged with the elastic force of the elastic member e2. In this state, the top end t4 of the second opposite member 82 is made to come in contact with the reference surface r1, whereby the height of the reference plate 822 becomes the same height with the reference surface r1. That is, the reference plate 822 is arranged on the colorimetry region a1.

The reference plate 822 is, for example, a ceramic plate with a uniform color, and its color values (for example, color data of the XYZ color system) have been known, and, are memorized in the memory 20. The spectral colorimeter 70 performs the colorimetry for the reference plate 822, compares the colorimetry data with the color values of the reference plate, thereby performing the calibration for the spectral colorimeter 70.

(Third Opposite Member 83)

Figure 12:
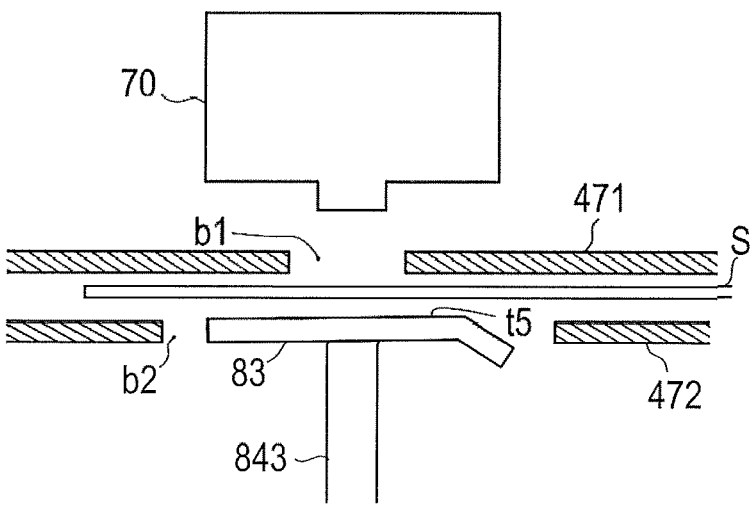
FIG. 12 is an illustration showing a third opposite member at an opposite position.

FIG. 12 is an illustration showing the third opposite member 83 located at the opposite position for the spectral colorimeter 70. In FIG. 12, the height of the top end t5 of the third opposite member 83 is substantially the same height as the conveyance surface of the second guide plate 472. The third opposite member 83 placed at the opposite position closes the opening b2 of the second guide plate 472, and guides the conveyance of the sheet S. During not performing the colorimetry without using the spectral colorimeter 70, the first opposite member 81 is retracted and the third opposite member 83 is disposed at the opposite position.

(Control for the Reading Apparatus 102)

Figure 13:
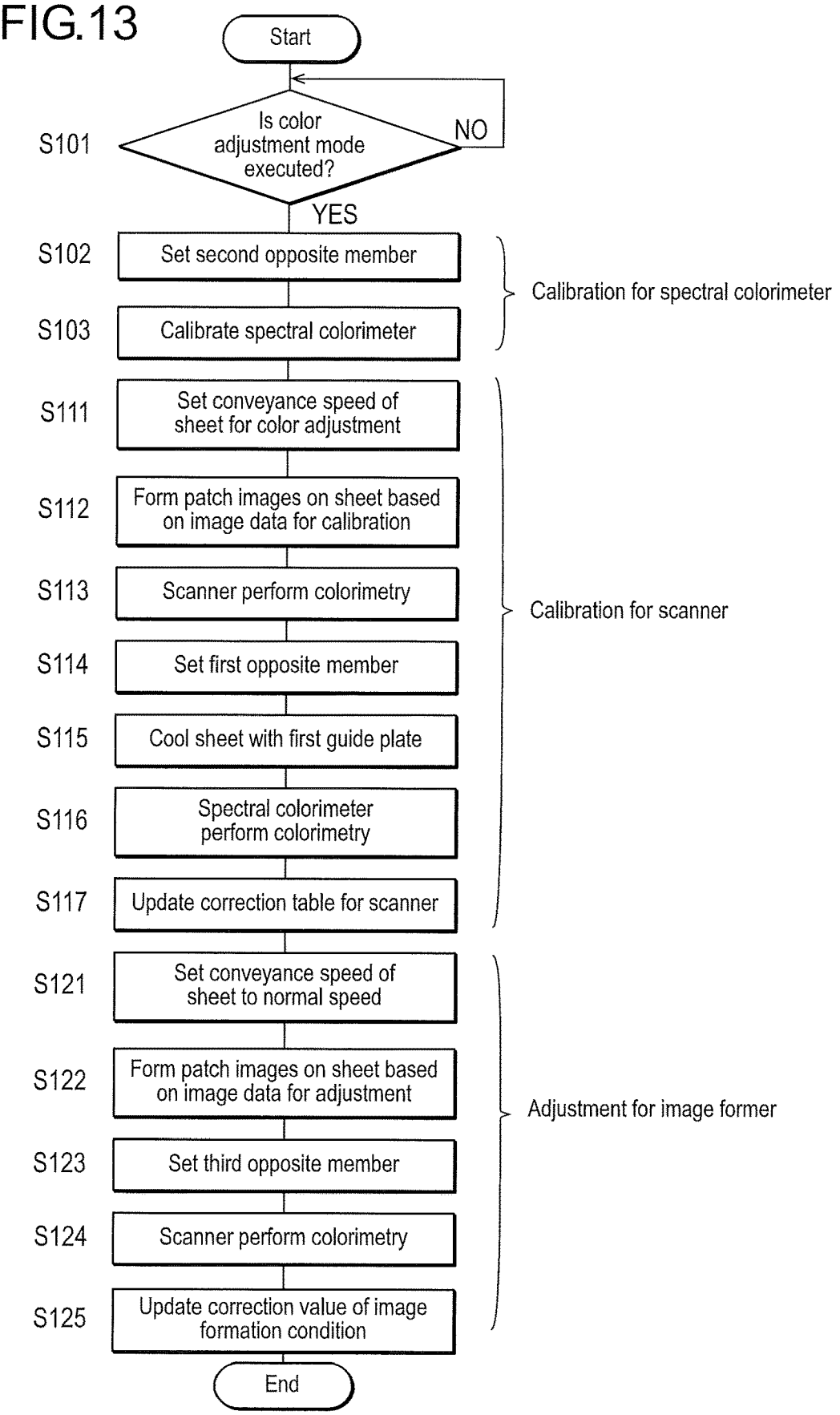
FIG. 13 is a flow chart showing control for a reading apparatus.

Next, with reference to the flowchart shown in FIG. 13, the control for the reading apparatus 102 according to the present embodiment is described.

First, the processor 10 determines whether a color adjustment mode is to be executed (S101). For example, the execution timing of the color adjustment mode may be set so as to execute for each time before starting the execution of a print job, or, may be set so as to execute for each time when a predetermined period (for example, 24h) elapses. The setting of this execution timing is memorized in the memory 20. In the case where the color adjustment mode is executed (S101: YES), the processing will be advanced to the next.

(Calibration for the Spectral Colorimeter 70)

Next, the second opposite member 82 is set at the pressing position (S102). In concrete terms, the processor 10 controls the member shifter 85 so as to rotate and shift the second opposite member 82 to the opposite position for the spectral colorimeter 70, to shift it upward toward the first guide plate 471, and to arrange the reference plate 822 of the second opposite member 82 on the colorimetry region a1 (refer to FIG. 11).

Next, the processor 10 performs the calibration for the spectral colorimeter 70 (S103). In concrete terms, the spectral colorimeter 70 performs the colorimetry for the reference plate 822 located on the colorimetry region a1, the obtained colorimetry data is compared with the color values of the reference plate read from the memory 20, and correction is performed in accordance with a difference in the comparison, whereby the calibration for the spectral colorimeter 70 is performed.

(Calibration for the Scanner 60a)

Next, the processor 10 sets the conveyance speed of the sheet S in the reading apparatus 102 to a conveyance speed for color adjustment (S111). The conveyance speed for color adjustment is slower than the conveyance speed at the time of the normal printing. The conveyance speed for color adjustment may be set to, for example, 490 mm/sec.

Subsequently, patch images of a plurality of colors are formed on a sheet S by the image former 30 by using image data for calibration memorized in the memory 20 (S112). A plurality of patch images is formed at a position corresponding, in the width direction, to the colorimetry region a1 of the spectral colorimeter 70, for example, at the central position in the width direction. Moreover, it is preferable that the plurality of colors of the patch images are distributed over the entire color gamut capable of being output by the image former 30.

Next, the scanner 60b performs the colorimetry for the patch images formed on the sheet S in Step S112 (S113).

Next, the first opposite member 81 is set at the pressing position (S114). In concrete terms, the processor 10 controls the member shifter 85 so as to rotate and shift the first opposite member 81 to the opposite position for the spectral colorimeter 70, to shift the first opposite member 81 upward toward the first guide plate 471, and to bring the first opposite member 81 in contact with the first guide plate 471 (refer to FIG. 8).

Next, a sheet S is conveyed to the colorimetry region a1, and the sheet S is cooled with the first guide plate 471 (S115). The conveyed sheet S enters between the first opposite member 81 and the first guide plate 471 against the elastic force of the elastic member e1. At this time, the sheet S is conveyed in a state of being brought in contact with the reference surface r1 of the first guide plate 471. With this, the conveyed sheet S comes in contact with the reference surface r1 located on the upstream side than the colorimetry region a1 of the first guide plate 471, whereby the heat energy of the sheet S is taken off by the first guide plate 471 through heat conduction. With this, even if the sheet S has been heated in the fixer 36, by the time when the sheet S reaches the colorimetry region a1, the sheet S is sufficiently cooled, and its temperature lowers (for example, to 30 degrees or less).

The spectral colorimeter 70 performs the colorimetry for the patch images formed in Step S112 on the sheet S (S116). At this time, since the sheet S has been sufficiently cooled in Step S115, there is almost no influence of thermochromism, and it becomes possible to perform accurate color measurement.

Next, by comparing the colorimetry results in Step S113 and Step S116, the correction table for the scanner 60b is updated (S117). This correction table is, for example, a multidimensional LUT (look-up table) to convert the read-out signals of the scanner 60b into color data.

(Adjustment for the Image Former 30)

Next, the processor 10 sets the conveyance speed of the sheet S in the reading apparatus 102 to the conveyance speed at the time of the normal printing (S121).

Thereafter, the patch images of a plurality of colors are formed on a sheet S by the image fouler 30 by using the image data for adjustment memorized in the memory 20 (S122). The plurality of patch images is those in which, for example, image densities are changed in multiple stages for each basic color over the entire surface of the sheet S.

Next, the third opposite member 83 is set (S123). In concrete terms, the processor 10 controls the member shifter 85 so as to rotate and shift the third opposite member 83 to the opposite position for the spectral colorimeter 70 (refer to FIG. 12). This is performed for preventing the poor conveyance due to the collision of the tip of the sheet S with the edge of the opening b2 of the second guide plate 472.

Next, the scanner 60b performs the colorimetry for the patch images formed in Step S122 on the sheet S (S124).

Next, on the basis of the colorimetry result in Step S124, the processor 10 adjusts the image formation conditions in the image former 30, for example, the output of the writer 34 and the output of the development bias applied to the developing roller of the developer 33 (S125), and, ends the processing (End).

As described above, according to the processing in the flow chart shown in FIG. 13, the sheet S is conveyed to the colorimetry region a1 in the state where the sheet S is brought in contact with the reference surface r1 of the first guide plate 471 by the first opposite member 81, whereby it is possible to sufficiently cool the sheet S until the sheet S reaches the colorimetry region a1. With this, it becomes possible to perform the colorimetry by the spectral colorimeter 70 stably with high accuracy without the influence of thermochromism.

It should be noted that in the flowchart shown in FIG. 13, one or more steps may be omitted, or repeated, and/or one or more steps may be performed in a different order from the order shown in FIG. 13. For example, the setting (S114) of the first opposite member 81 may be performed immediately after the calibration for the spectral colorimeter 70.

Moreover, before performing the color measurement (S113) with the scanner 60b, shading correction may be performed by the back surface unit 69b. Furthermore, the correction table for the scanner 60b updated in Step S117 may be applied also to the scanner 60a as it is, or, the correction table for the scanner 60a may be calculated on the basis of the correction table for the scanner 60b. Moreover, the conveyance speed for color adjustment set in Step S111 may be applied simultaneously also to the image forming apparatus 101. Furthermore, the conveyance speed for the color adjustment may be set such that the temperature of the sheet S having reached the colorimetry region a1 becomes 30 degrees or less at which the influence of a thermochromism phenomenon can be disregarded. As a conveyance speed becomes slower, a time during which the sheet S comes in surface contact with the reference surface r1 of the first guide plate 471, becomes longer. That is, since the cool time becomes longer, the temperature of the sheet S at a time point when having reached the colorimetry region a1 becomes lower.

(Opening and Closing Mechanism 48)

Next, with reference to FIG. 14A, FIG. 14B, FIG. 15A, and FIG. 15B, the opening and closing mechanism 48 of the reading apparatus 102 is described. With the opening and closing mechanism 48 described below, for example, when the processing for conveyance jam is performed, the conveyance path 42b is opened so that a user can access.

Figure 14A:
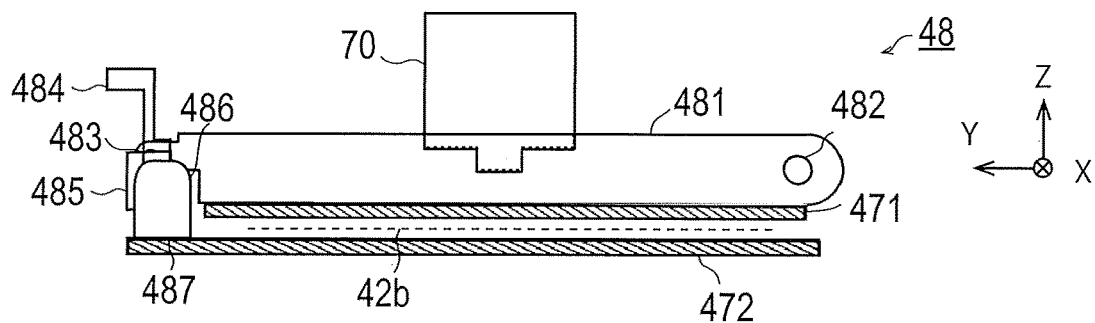
FIG. 14A is an illustration showing a periphery of a conveyance path in a normal state viewed from an X direction.
Figure 14B:
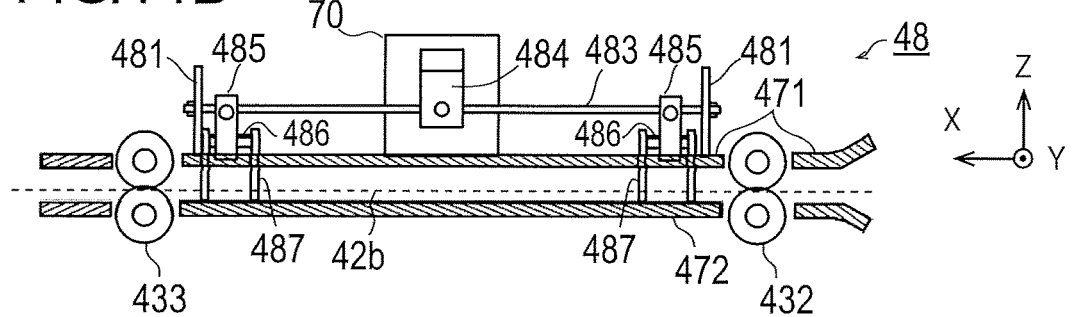
FIG. 14B is an illustration showing a periphery of a conveyance path in a normal state viewed from a Y direction.

FIG. 14A and FIG. 14B each is an illustration showing the periphery of the conveyance path 42b in a normal state. As shown in these figures, the opening and closing mechanism 48 includes a pair of side panels 481 attached to the first guide plate 471, a rotation shaft 482, a shaft 483, a handle 484, a hook 485, and a panel 487 and a fixed shaft 486 attached to the second guide plate 472.

To the near side (the Y direction) of the pair of side panels 481, the shaft 483 extended to exist in the X direction is attached, and the handle 484 and the hook 485 are attached to this shaft 483. Moreover, to the rear side of the pair of side panels 481, the rotation shaft 482 extended to exist in the X direction is attached. This rotation shaft 482 is supported by the casing of the reading apparatus 102, and respective members attached to the first guide plate 471 and the side panel 481 pivot on the rotation shaft 482 serving as a rotation center. The respective members are urged upward (clockwise in FIG. 14A) around the rotation shaft 483 by a spring (not shown), and in the normal state, the tip of the hook 485 is engaged with the fixed shaft 486.

The hook 485 is disengaged from the fixed shaft 486 by operating the handle 484 by a user. Successively, after the hook 485 has been disengaged from the fixed shaft 486, the respective members are lifted upward so as to pivot on the rotation shaft 482 serving as a rotation center. By making them pivot upward, the conveyance path 42b is made into an opened state.

Figure 15A:
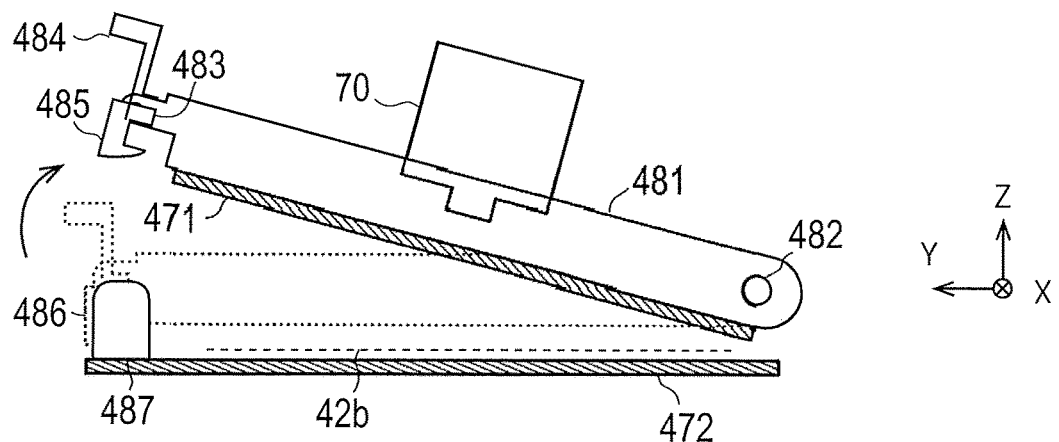
FIG. 15A is an illustration showing a periphery of a conveyance path in an opened state viewed from an X direction.
Figure 15B:
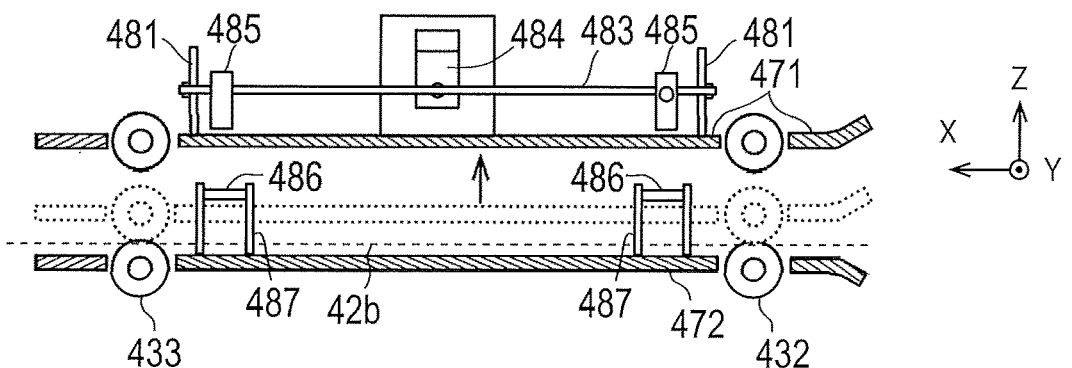
FIG. 15B is an illustration showing a periphery of a conveyance path in an opened state viewed from an Y direction.

FIG. 15A and FIG. 15B each an illustration showing the periphery of the conveyance path 42b in the opened state. In this opened state, the spectral colorimeter 70 and the upper roller of each of the conveyance rollers 432 and 433 have been also lifted upward together with the first guide plate 471 as one body. Accordingly, it becomes possible for a user to access easily the opened conveyance path 42b. In this connection, in the present embodiment, by moving upwardly the respective members on the first guide plate 471 side, the conveyance path 42b has been opened. However, without restricting to the above manner, the conveyance path 42b may be configured to be opened by moving only the second guide plate 472 side, or both of the second guide plates 471 and 472.

(Second and Third Embodiments)

In the reading apparatus 102 of the first embodiment shown in FIG. 1 to FIG. 12, the first guide plate 471 with which a sheet S is brought in contact by being urged by the first opposite member 81, is provided to over the entire conveyance region of a sheet in the width direction, and the first guide plate 471 is a part of the guide on the upstream side than the colorimetry region a1 of the reading apparatus 102 in the conveyance direction.

On the contrary, in the second embodiment described below, a first guide plate 475 is provided to only a part of the region in the width direction. In the third embodiment, a first guide plate 478 is provided over the entire region of the sheet conveyance region of a sheet in the width direction, and the first guide plate 478 is all of the guide on the upstream side than the colorimetry region a1 of the reading apparatus 102 in the conveyance direction.

Hereinafter, with reference to FIG. 16 through FIG. 18, the second embodiment will be described, and thereafter, with reference to FIG. 19, the third embodiment will be described.

Figure 16:
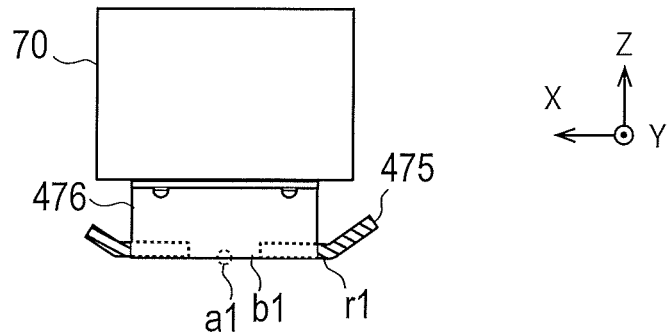
FIG. 16 is a side view showing a first guide plate in the second embodiment.
Figure 17:
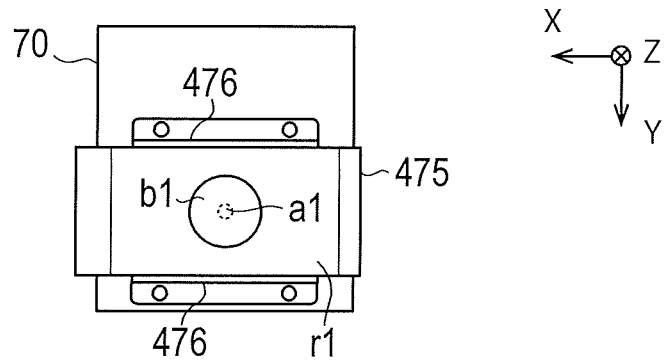
FIG. 17 is a bottom view of a first guide plate.

FIG. 16 is a side view showing the spectral colorimeter 70 and the first guide plate 475 of the reading apparatus 102 according to the second embodiment, and FIG. 17 is the bottom view thereof. FIG. 18 is an illustration showing the arrangement position of the first guide plate 475 with respect to the first opposite member 81 located in the pressing position.

As shown in FIG. 16 and FIG. 17, the first guide plate 475 is attached to the casing of the spectral colorimeter 70 via a pair of side plates 476 with screws. The side plate 476 and the first guide plate 475 may be constituted in one body with a metal plate made of metal with high heat conductivity.

Figure 18:
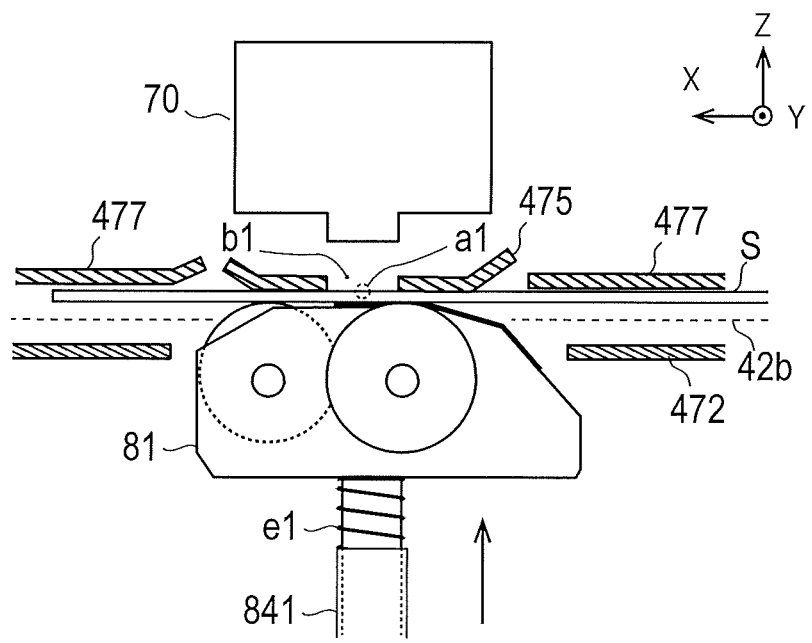
FIG. 18 is an illustration showing an arrangement position of a first guide plate with respect to a first opposite member at a pressing position.

As shown in FIG. 18, in the reading apparatus 102 according to the second embodiment, there are provided the first guide plate 475 and the third guide plate 477 as an upper guide along the conveyance path 42b. The first guide plate 475 equipped with the reference surface r1 is disposed only on a portion corresponding to the spectral colorimeter 70 in the width direction and in the conveyance direction. The third guide plate 477 has almost the same height (the XY plane) as the first guide plate 475, and, is disposed so as to surround the first guide plate 475.

As shown in these figures, similarly to the first embodiment shown in FIG. 5 and the like mentioned above, the first guide plate 475 is provided with the opening b1 with a diameter of, for example, 30 mm. The undersurface of the first guide plate 475 is the reference surface r1 parallel to the conveyance path 42b, and the area (except the opening b1) of the reference surface r1 is about 1500 mm$^2$. As the area of this reference surface r1 is increased, since the contact area with a sheet S becomes larger, the cooling performance increases. However, it becomes difficult to attach the reference surface r1 to the spectral colorimeter 70 with sufficient accuracy. In the second embodiment, in consideration of various conditions, the area of the reference surface r1 is set such that the temperature of a sheet S at the time of reaching the colorimetry region a1 becomes 30 degrees or less. Examples of the various conditions include the conveyance speed of a sheet at the time of color adjustment, a distance (time) from the fixer 36 to the colorimetry region a1, a contact region formed on the first guide plate 471, and, a contact area between a sheet S and the reference surface r1.

In this way, also in the reading apparatus 102 according to the second embodiment, similarly to the first embodiment, it becomes possible to cool quickly a sheet S with residual heat provided by the fixer 36 through heat conduction, and to lower the temperature of the sheet S to 30 degrees or less at the time of performing the colorimetry. With this, it becomes possible to perform the colorimetry by the spectral colorimeter 70 stably with high accuracy without the influence of thermochromism. Moreover, in the second embodiment, since the first guide plate 475 is directly attached to the spectral colorimeter 70, the positional accuracy in the height direction (the Z direction) of the reference surface r1 can be secured easily.

Figure 19:
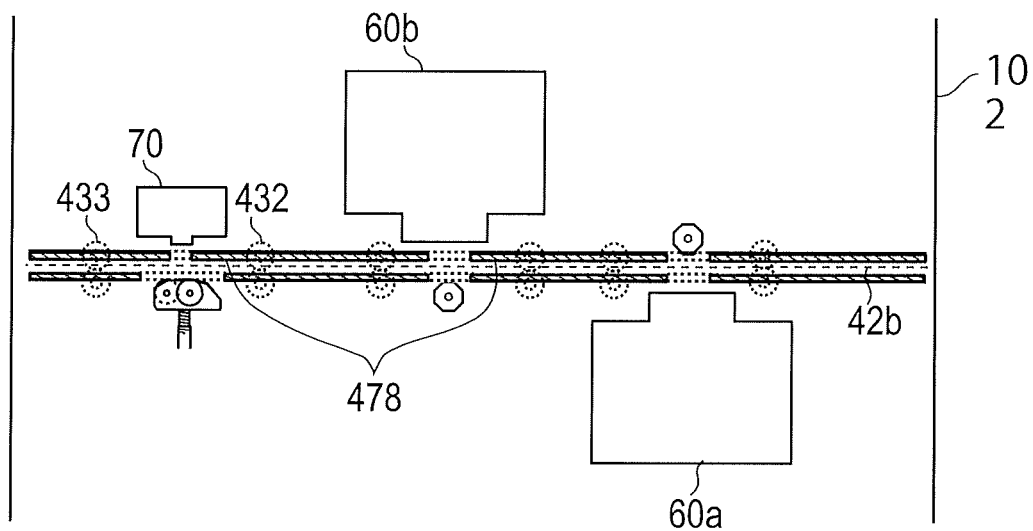
FIG. 19 is an illustration showing a first guide plate in the third embodiment.

The first guide plate 478 of the reading apparatus 102 shown in FIG. 19 according to the third embodiment is disposed over the entire region of the conveyance region of a sheet S in the width direction, and, is disposed along the all the entire region of the conveyance path 42b of the reading apparatus 102 also in the conveyance direction. In this connection, in the conveyance direction, the first guide plate 478 may be disposed along the entire region on the upstream side than the colorimetry region a1.

In this way, by using the first guide plate 478 with a large area, at the time of the colorimetry by the spectral colorimeter 70, it becomes possible to bring the first guide plate 478 in surface contact with a sheet S to be conveyed to the colorimetry region a1 with the large area. That is, the cooling region can be made larger, and a sheet S can be cooled more efficiently.

MODIFIED EXAMPLE

The above-described embodiments intend to exemplify the summary of the present invention, and, does not intend to limit the present invention. Many substitutes, revisions, and modifications are clear for a person skilled in the art. For example, the modified examples described below may be applied to the first to third embodiments.

First Modified Example

Figure 20:
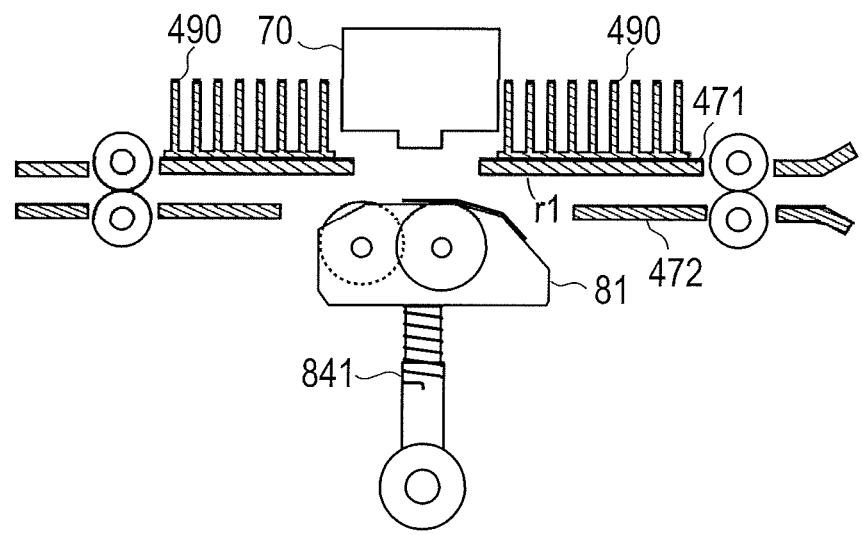
FIG. 20 is an illustration showing a constitution of a periphery of a first guide plate in the first modified example.

FIG. 20 is an illustration showing the constitution of the periphery of the first guide plate 471 according to the first modified example. In the example shown in FIG. 20, to the surface of the first guide plate 471 opposite to the reference surface r1, cooling fins 490 for cooling of the first guide plate 471 are attached with adhesives with high heat conductivity. When the first guide plate 471 cools a sheet S, even if its temperature rises with heat taken from the sheet S, it becomes possible to lower the temperature to near the room temperature immediately with the cooling fins 490. In this connection, the cooling fins 490 may be applied to the first guide plate in the second and third embodiments. Moreover, in place of the cooling fin 490, or together with the cooling fin 490, a cooling fan may be adopted.

Second Modified Example

Figures 21, 22:
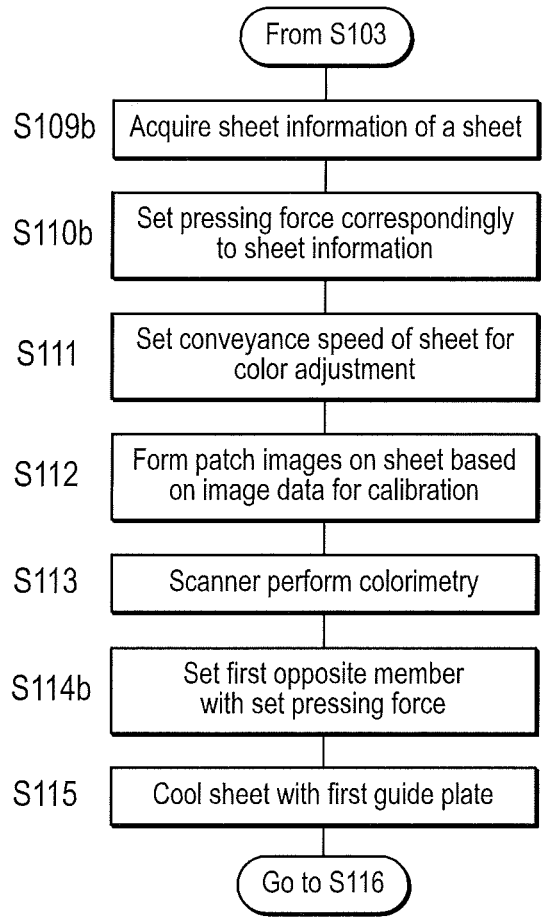
FIG. 21 is a flowchart showing control for a reading apparatus according to the second modified example.
FIG. 22 is a diagram showing an example of a control table.

Next, with reference to FIG. 21 and FIG. 22, the reading apparatus 102 in the second modified example is described. In the second modified example, the pressing force by the first opposite member 81 is changed accordingly to the sheet information of a sheet S to be subjected to the colorimetry.

FIG. 21 is a flowchart showing the control executed by the reading apparatus 102 according to the second modified example. The flowchart shown in FIG. 21 is performed between Step S103 and Step S116 shown in FIG. 13. Moreover, the same process as that in FIG. 13 is provided with the same code, thereby omitting a part of the description.

First, the sheet information of a sheet is acquired. (S109$b$). In this step, for example, in the case of using the same sheet as that in a print job scheduled to be executed, the sheet information of the sheet to be used is acquired. The calibration for the scanner 60$b$ by using the same sheet as the print job is performed for increasing calibration accuracy.

On the assumption that "the thickness of sheet" is used as the sheet information, the following examples are described. The processor 10 reads out "the thickness of sheet" correlated with the sheet feed tray 41 from the memory 20.

The setting of the pressing force is performed correspondingly to the sheet information acquired in Step S109$b$ (S110$b$). The control table showing the correspondence between the sheet information and the pressing force has been memorized beforehand in the memory 20. FIG. 22 shows an example of the control table. As shown in FIG. 22, in the case where the thickness of sheet is 100 μm, the pressing force is set to 2.05 N. The setting of the pressing force can be performed by changing the amount of rising of the holding member 84 by the member shifter 85. By changing the height of the rotation shaft 840 (refer to FIG. 3), since the amount of deflection of the elastic member e1 (for example, spring) changes, the pressing force (urging force) to the sheet S by the first opposite member 81 changes. The relationship between the pressing force and an amount of rising is memorized beforehand in the memory 20.

Henceforth, similarly to FIG. 13, the processing in each of Steps S111 to S113 is performed, and next, the first opposite member 81 is set with the pressing force (the amount of rising) set in Step S110 (S114$b$).

Successively, the sheet S is conveyed to the colorimetry region a1, and, is urged toward and brought in contact with the reference surface r1 of the first guide plate 471 with the set pressing force, thereby performing cooling for the sheet S (S115). Henceforth, the processing is returned to Step S116 in FIG. 8, and, is ended.

It should be noted that as the sheet information, in addition to "the thickness of sheet", the basis weight of sheet, the size of sheet, the kind (coated sheet) of sheet, etc. may be used. As the basis weight of sheet is larger, or the size of sheet is larger, the pressing force is made larger. That is, since the amount of residual heat (the amount of heat energy) accumulated in a sheet S becomes larger correspondingly to these factors, it is necessary to cool the sheet S more. Moreover, in the case where the kind of sheet is a coated sheet, compared with a regular sheet, the pressing force is made small. In the case where the sheet S is a coated sheet, its surface is smoother than a regular sheet. Accordingly, the surface of the sheet coming in contact with the reference surface r1 of the first guide plate 471 becomes larger, and cooling can be performed efficiently.

As mentioned above, in the second modified example, since the pressing force is changed correspondingly to the sheet information, it becomes possible to perform cooling for a conveyed sheet with the appropriate condition. Accordingly, it becomes possible to perform the colorimetry by the spectral colorimeter 70 stably with high accuracy without the influence of thermochromism.

Other Modified Examples

Moreover, physically, as long as the processor 10 (and memory 20) is in the image forming system 100, the processor 10 may be arranged in any of the image forming apparatus 101, the reading apparatus 102, and the post processing apparatus 103. Alternatively, the processor 10 is disposed in a plurality of apparatuses among them, and the whole image forming system 100 may be controlled by the cooperation of them. For example, the control flow shown in each of FIG. 13 and FIG. 21 has been described as being executed by the processor 10 of the image forming system. However, the processor 10 may be disposed for the both sides of the reading apparatus 102 and the image foaming apparatus 101, and the processor 10 in the reading apparatus 102 may serve as a main processor, may cooperate with the processor 10 in the image forming apparatus 101, and may perform these processes.

Furthermore, the description has been given for the case where an electrophotographying system is used as the image former 30. However, without restricting to the above case, an image former of an inkjet system equipped with a dryer to heat a sheet having been subjected to image formation with ink may be applied. Moreover, in the example shown in the above, as the colorimetry unit disposed to face the first guide plate 471 and the first opposite member 81, the spectral colorimeter 70 has been used. However, the scanner 60*b* may be used.

Procedures and methods that perform various kinds of processing in the image forming system and the reading apparatus according to the above-mentioned embodiments can be realized by any of a dedicated hardware circuit and a programmed computer. The above-mentioned program, for example, may be provided by a computer-readable recording medium, such as CD-ROM (Compact Disc Read Only Memory), or may be provided on-line through networks, such as the Internet. In this case, the program recorded in the computer-readable recording medium is usually transferred and memorized in a memory, such as a hard disk. Moreover, the above-described program may be provided as independent application software, or, may be included as one function of an image forming apparatus in the software of the apparatus.

Although embodiments of the present invention have been described and illustrated in detail, the disclosed embodiments are made for purpose of illustration and example only and not limitation The scope of the present invention should be interpreted by terms of the appended claims.

What is claimed is:

1. A reading apparatus that performs colorimetry for a sheet, having a front surface with a print surface on which an image is printed and a back surface opposite the front surface, the reading apparatus comprising:
   a conveyor that conveys the sheet along a conveyance path;
   a first guide member that includes a reference surface arranged to face the conveyance path and to oppose the print surface of the sheet and provided with an opening, and, guides the sheet conveyed on the conveyance path;
   a first opposite member that urges the sheet being conveyed on the conveyance path toward the reference surface, and, brings the front surface of the sheet in contact with the reference surface by the first opposite member pressing the back surface of the sheet; and
   a colorimetry unit that is disposed to face the first guide member at a side opposite to the conveyance path via the first guide member, and, performs colorimetry at a colorimetry region within the opening for the image on the front surface of the sheet brought in contact with the reference surface, wherein
   the first opposite member is urged and brought in contact with the first guide member before the conveyed sheet enters between the first opposite member and the first guide member, and
   the reference surface of the first guide member comes in contact with the sheet urged by the first opposite member and cools the sheet when the sheet is conveyed to the colorimetry region.

2. The reading apparatus of claim 1, further comprising:
   a second opposite member including a reference plate for color calibration, and
   a member shifter that switches over the first opposite member and the second opposite member selectively,
   wherein when performing calibration for the colorimetry unit, the member shifter shifts and brings the second opposite member in contact with the reference surface so that the reference plate is located on the colorimetry region within the opening.

3. The reading apparatus of claim 1, further comprising:
   a second guide member disposed at a side opposite to the first guide member so as to sandwich the conveyance path,
   wherein the first opposite member shifts toward the reference surface of the first guide member through an opening provided to the second guide member so that the first opposite member urges and brings the sheet being conveyed in contact with the reference surface.

4. The reading apparatus of claim 3, further comprising:
   an opening and closing mechanism that shifts at least one of the first guide member and the second guide member,
   wherein at least one of the first guide member and the second guide member is shifted by the opening and closing mechanism so that the conveyance path is opened so as to make a user accessible.

5. The reading apparatus of claim 1, wherein the first opposite member includes at least three rollers driven to rotate, and an outer peripheral surface of each of the rollers comes in point contact with the sheet being conveyed so that the sheet is urged and brought in contact with the reference surface.

6. The reading apparatus of claim 1, wherein an urging force toward the reference surface of the first guide member by the first opposite member is changed in accordance with sheet information of the sheet being conveyed.

7. The reading apparatus of claim 1, wherein the first opposite member is able to shift to a pressing position to urge the sheet being conveyed toward the reference surface and a retracted position not to urge the sheet being conveyed, and the first opposite member is set at the pressing position in a reading mode to perform colorimetry for the sheet by the colorimetry unit, and is set at the retracted position in a non-reading mode not to perform colorimetry.

8. The reading apparatus of claim 1, wherein the first guide member is disposed only on a part of a region in a width direction orthogonal to a conveyance direction of the sheet, and, is attached to the colorimetry unit.

9. The reading apparatus of claim 1, wherein the first guide member is disposed on an entire region of a conveyance region of the sheet in a width direction orthogonal to a conveyance direction, and the first guide member is all or a part of a guide member on an upstream side in the conveyance direction than a colorimetry region within the opening of the reading apparatus.

10. The reading apparatus of claim 1, wherein the first guide member is provided with a cooling fin.

11. An image forming system, comprising:
    an image forming apparatus that prints an image on a print surface of a sheet, the print surface being a front surface of the sheet and the sheet comprising a back surface opposite the front surface; and
    a reading apparatus that performs colorimetry for the sheet output from the image forming apparatus with the print surface on which the image is printed by the image forming apparatus, the reading apparatus including:
    a conveyor that conveys the sheet output from the image forming apparatus along a conveyance path;
    a first guide member that includes a reference surface arranged to face the conveyance path and to oppose the print surface of the sheet and provided with an opening, and, guides the sheet conveyed on the conveyance path;
    a first opposite member that urges the sheet being conveyed on the conveyance path toward the reference surface, and, brings the front surface of the sheet in contact with the reference surface by the first opposite member pressing the back surface of the sheet; and a colorimetry unit that is disposed to face the first guide member at a side opposite to the conveyance path via the first guide member, and, performs colorimetry at a colorimetry region within the opening for the image on the front surface of the sheet brought in contact with the reference surface, wherein the first opposite member is urged and brought in contact with the first guide member before the conveyed sheet enters between the first opposite member and the first guide member, and the reference surface of the first guide member comes in contact with the sheet urged by the first opposite member and cools the sheet when the sheet is conveyed to the colorimetry region.

12. The image forming system of claim 11, wherein the reading apparatus further includes a second opposite member including a reference plate for color calibration, and a member shifter that switches over the first opposite member and the second opposite member selectively, wherein when performing calibration for the colorimetry unit, the member shifter shifts and brings the second opposite member in contact with the reference surface so that the reference plate is located on the colorimetry region within the opening.

13. The image forming system of claim 11, wherein the colorimetry unit is a spectral colorimeter, the reading apparatus further includes a scanner capable of performing colorimetry for the image on an entire width of a conveyance region of a sheet in a width direction orthogonal to a conveyance direction of the sheet, each of the colorimetry unit and the scanner performs colorimetry for the identical image on the conveyed sheet, and a correction amount for the scanner is determined on a basis of obtained colorimetry data.

14. A non-transitory computer-readable storage medium storing a control program for a reading apparatus that includes a conveyor that conveys a sheet along a conveyance path; a first guide member that includes a reference surface and provided with an opening, and, guides the sheet conveyed on the conveyance path, the sheet possessing a front surface and a back surface opposite the front surface; a first opposite member that urges the sheet being conveyed on the conveyance path toward the reference surface, and, brings the front surface of the sheet in contact with the reference surface by the first opposite member pressing the back surface of the sheet; and a colorimetry unit that is disposed to face the first guide member at a side opposite to the conveyance path via the first guide member, and, performs colorimetry at a colorimetry region within the opening for the image through the opening, the control program making a computer execute processing comprising:

(a) conveying the sheet on which an image is printed on the front surface of the sheet;

(b) bringing the first guide member in contact with the first opposite member; and (c) performing colorimetry at the colorimetry region within the opening for the image on the front surface of the sheet brought in contact with the reference surface, wherein the reference surface of the first guide member comes in contact with the sheet urged by the first opposite member and cools the sheet when the sheet is conveyed to the colorimetry region.

15. The non-transitory computer-readable storage medium of claim 14, wherein the colorimetry unit is a spectral colorimeter, the reading apparatus further includes a scanner capable of performing colorimetry for an image on an entire region of the sheet in a width direction orthogonal to a conveyance direction of the sheet, and wherein the processing further comprises:

(d) performing colorimetry for the image on the front surface of the sheet with the scanner after (a); and (e) determining a correction amount for the scanner on a basis of colorimetry data acquired by performing colorimetry for an identical image in (c) and (d).

16. The non-transitory computer-readable storage medium of claim 14, the processing further comprising:

(f) acquiring sheet information of the sheet to be conveyed before (b), and, setting a pressing force of the first opposite member on a basis of the acquired sheet information, wherein in (b), the sheet conveyed on the conveyance path is conveyed in a state of being brought in contact with the reference surface by the first opposite member with a pressing force set in (f), and, is conveyed to the colorimetry region.

17. The reading apparatus of claim 1, wherein the first guide member is a flat metal plate.

18. The reading apparatus of claim 17, wherein the flat metal plate is a stainless steel material with a heat conductivity of 20.9 (W/m/K) or more.

19. The image forming system of claim 11, wherein the first guide member is a flat metal plate.

20. The image forming system of claim 19, wherein the flat metal plate is a stainless steel material with a heat conductivity of 20.9 (W/m/K) or more.

* * * * *